US012740748B2

(12) United States Patent
Thedeby et al.

(10) Patent No.: US 12,740,748 B2
(45) Date of Patent: Sep. 22, 2026

(54) MONITORING DEVICE AND A DATA COLLECTOR ASSEMBLY

(71) Applicant: LINXENS HOLDING SAS, Mantes la Jolie (FR)

(72) Inventors: Fredrik Thedeby, Mellbystrand (SE); Peter Nilsson, Farhult (SE); Lasse Bay, København NV (DK)

(73) Assignee: LINXENS HOLDING SAS, Mantes la Jolie (FR)

( * ) Notice: Subject to any disclaimer, the term of this patent is extended or adjusted under 35 U.S.C. 154(b) by 320 days.

(21) Appl. No.: 18/561,371

(22) PCT Filed: May 18, 2022

(86) PCT No.: PCT/EP2022/063490

§ 371 (c)(1),
(2) Date: Nov. 16, 2023

(87) PCT Pub. No.: WO2022/243394

PCT Pub. Date: Nov. 24, 2022

(65) Prior Publication Data

US 2024/0245356 A1 Jul. 25, 2024

(30) Foreign Application Priority Data

May 20, 2021 (DK) .................................. 202170259

(51) Int. Cl.
*A61B 5/05* (2021.01)
*A61B 5/00* (2006.01)
(Continued)

(52) U.S. Cl.
CPC ............ *A61B 5/6832* (2013.01); *A61B 5/257* (2021.01); *A61B 5/274* (2021.01); *A61B 2562/227* (2013.01)

(58) Field of Classification Search
CPC ..... A61B 5/282; A61B 5/6824; A61B 5/0006; A61B 5/1118; A61B 2560/0412;
(Continued)

(56) References Cited

U.S. PATENT DOCUMENTS 11,327,443 B1 * 5/2022 Trapero Martin . G04B 37/1413
2008/0288026 A1 11/2008 Cross et al.
(Continued)

FOREIGN PATENT DOCUMENTS

CN 104768450 A 7/2015
CN 108348185 A 7/2018
(Continued)

OTHER PUBLICATIONS

International Search Report dated Sep. 19, 2022 (4 pages) from PCT Priority Application PCT/EP2022/063490.
(Continued)

*Primary Examiner* — Joseph A Stoklosa
*Assistant Examiner* — Brian M Antiskay
(74) *Attorney, Agent, or Firm* — Crowell & Moring LLP

(57) ABSTRACT

A monitoring device including a data collector having a first sheet having a dermal side surface, a housing having a first electrical coupling area and first connector structures, a socket having a base and connected to the data col-lector, the socket having second connector structures connecting the socket to the housing via the first connector structures. The data collector includes a second sheet with a pattern of an electrically conductive material extending between a sensing portion of the data collector and an interface portion of the data collector that is arranged inside the socket, the interface portion having a second electrical coupling area for electrically connecting the first electrical coupling area with the sensing portion via the pattern of an electrically conductive material, and a sealing gasket extending around the
(Continued)

first and second electrical coupling areas. The sealing gasket contacts a first section of the interface portion.

12 Claims, 17 Drawing Sheets

(51) Int. Cl.
*A61B 5/257* (2021.01)
*A61B 5/274* (2021.01)

(58) Field of Classification Search
CPC ......... A61B 5/6833; A61B 5/25; A61B 5/318; A61B 5/308; A61B 2560/0468; A61B 5/287; A61B 5/6804; A61B 5/4806; G16H 40/67; G16H 20/30
USPC ......................... 600/372, 382–393, 508–509
See application file for complete search history.

(56) References Cited

U.S. PATENT DOCUMENTS

2012/0306662 A1* 12/2012 Vosch ...................... H04Q 9/00 340/870.07
2012/0310070 A1* 12/2012 Kumar ................... A61B 5/282 600/391
2014/0206977 A1* 7/2014 Bahney .................. A61B 5/257 600/386
2015/0087950 A1 3/2015 Felix et al.
2015/0181324 A1 6/2015 Hsieh et al.
2015/0250422 A1* 9/2015 Bay ...................... A61B 5/0533 600/391
2018/0125387 A1 5/2018 Hadley et al.
2018/0132733 A1 5/2018 Lai et al.
2019/0104961 A1 4/2019 Felix et al.
2019/0380615 A1 12/2019 Felix et al.
2020/0229706 A1* 7/2020 Nishimura ........... A61B 5/6832
2021/0030300 A1* 2/2021 Felix ...................... G16H 40/63

FOREIGN PATENT DOCUMENTS

| | | | |
|---|---|---|---|
| CN | 110621227 | A | 12/2019 |
| EP | 1 956 973 | A1 | 8/2008 |
| EP | 3 048 962 | A1 | 8/2016 |
| EP | 2 906 102 | B1 | 9/2017 |
| EP | 3 348 187 | A1 | 7/2018 |
| JP | 2011/170507 | A | 9/2011 |
| WO | WO 2007/063436 | A1 | 6/2007 |
| WO | WO 2007/083275 | A1 | 7/2007 |
| WO | WO 2015/048309 | A1 | 4/2015 |
| WO | WO 2021/216744 | A2 | 10/2021 |

OTHER PUBLICATIONS

International Preliminary Report on Patentability (1 page) dated Nov. 21, 2023 and appended Written Opinion of the International Searching Authority (10 pages) dated Sep. 19, 2022 from PCT Priority Application EP 2022/063490.
Search Report dated Nov. 12, 2021 (4 pages) from Danish Priority Application PA 2021 70259.
Additional Search Report dated Jan. 12, 2023 (2 pages) from Danish Priority Application PA 2021 70259.
Search Report dated Jan. 2, 2025 (6 pages) out of corresponding European Application No. 22 730 404.5.
Chinese-language Office Action issued in corresponding/parallel Chinese Application No. 202280035733.1 dated Aug. 1, 2026 (8 pages).

* cited by examiner

MONITORING DEVICE AND A DATA COLLECTOR ASSEMBLY

This application is a National Stage application of International Application No. PCT/EP2022/063490, filed May 18, 2022, the entire contents of which are incorporated herein by reference.

This application claims priority under 35 U.S.C. § 119(a) to Danish Patent Application No. PA 2021 70259, filed on May 20, 2021, the entire contents of each of which are incorporated herein by reference.

BACKGROUND OF THE INVENTION

Field of Invention

The present invention concerns a monitoring device with a housing and a data collector connected to the housing via a socket to define the monitoring device. The invention also concerns a data collector assembly for connection to a housing.

Description of the Related Art

WO2015/048309 and EP2906102 disclose examples of monitoring devices attachable to the skin of a person to be monitored, wherein from a data collector data captured by sensing portions are transferred to and collected in a housing via an interface of the monitoring device.

SUMMARY OF THE INVENTION

The present invention aims at providing an improved monitoring device that maintains the aforementioned interface sealed against the surroundings and which at the same time may be assembled by a user with a low manual effort.

Thus, according to the invention as broadly defined a sealing gasket extending around first and second electrical coupling areas is arranged to contact at least a first section of an interface portion of the data collector.

Preferred arrangements and configurations of the sealing gaskets are described herein. In one embodiment is the gasket mounted onto the interface portion, to extend around a coupling area defined by the interface portion, in the way that the gasket is a part of the data collector assembly.

A base of the socket connecting the data collector to the housing preferably has an open system of interconnected grooves on its lower face, opening up at the periphery of the base, to allow for any moisture transported from the skin of the monitored person through material layers constituting the data collector, to evaporate at the level of the base.

The interface portion may be defined by a material layer/sheet constituting the data collector and which may be manipulated relative to the remaining portions of the data collector when the latter is connected to the socket, in the way that the interface portion is turned more or less out of the general plane of the data collector and then brought to rest against an upper face of the base of the socket and secured in that position. In this way is the monitoring device interface located inside the socket, well protected against mechanical impacts and with the remaining portions of the data collector extending below the base of the socket.

The base preferably has an edge along its periphery, or the socket includes an upstanding peripheral wall that has a recess that defines a length of an edge along the periphery of the base. A transition to the interface portion preferably overlies a length of this peripheral edge. Using such a recess allows for the interface portion to be positioned on top of the base displaced only slightly inside the socket from its general contour.

Preferably, the interface portion, as well as the gasket, is secured to the base so as to be closer to first and second connector structures that define together a hinge for pivotal engagement of the housing with the socket. This allows for the gasket to be pressed very tightly against the opposing surface to ensure a very high degree of tightness as the housing is turned about the hinge to be locked to the socket by remaining connector structures engaging each other.

The invention will now be explained in further details with reference to presently preferred embodiments.

DETAILED DESCRIPTION

The invention will now be explained in more detail below by reference to preferred embodiments.

Figure 1A:
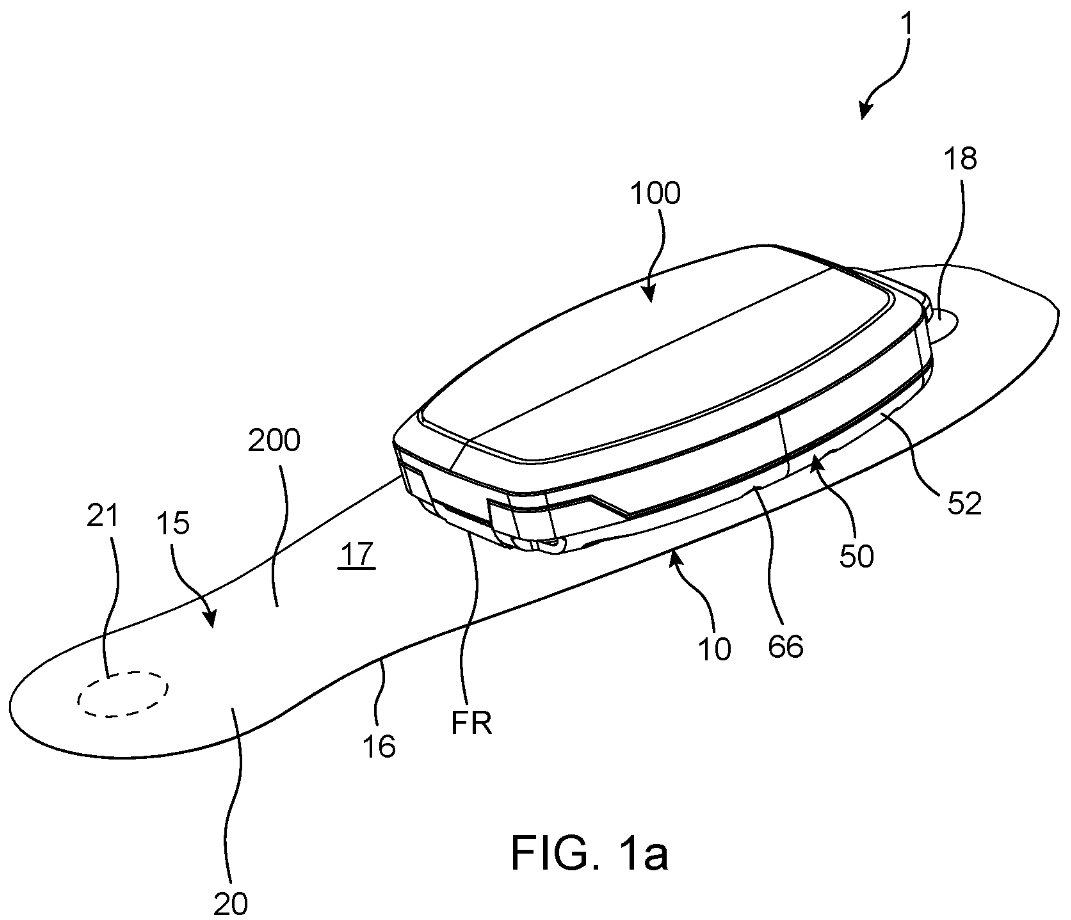
FIG. 1*a* shows a perspective top view of a first embodiment of a monitoring device of the present invention.

The person monitoring device 1 of the invention as shown in FIG. 1*a* generally is formed by assembling two parts, namely a first, disposable part for use for a relatively short time and defined by an elongated, flexible data collector 10 adhesively connected to a socket 50, and a second part defined by a housing 100 which typically includes a processor and/or other high cost electronics.

The data collector 10 has one or more sensing portions 18, 21 along its length, and via the socket 50 is the data collector 10 releasably connected to the housing 100 in a way to allow monitored data to be transferred to the housing 100 from the one or more sensing portions 18, 21.

Figure 1B:
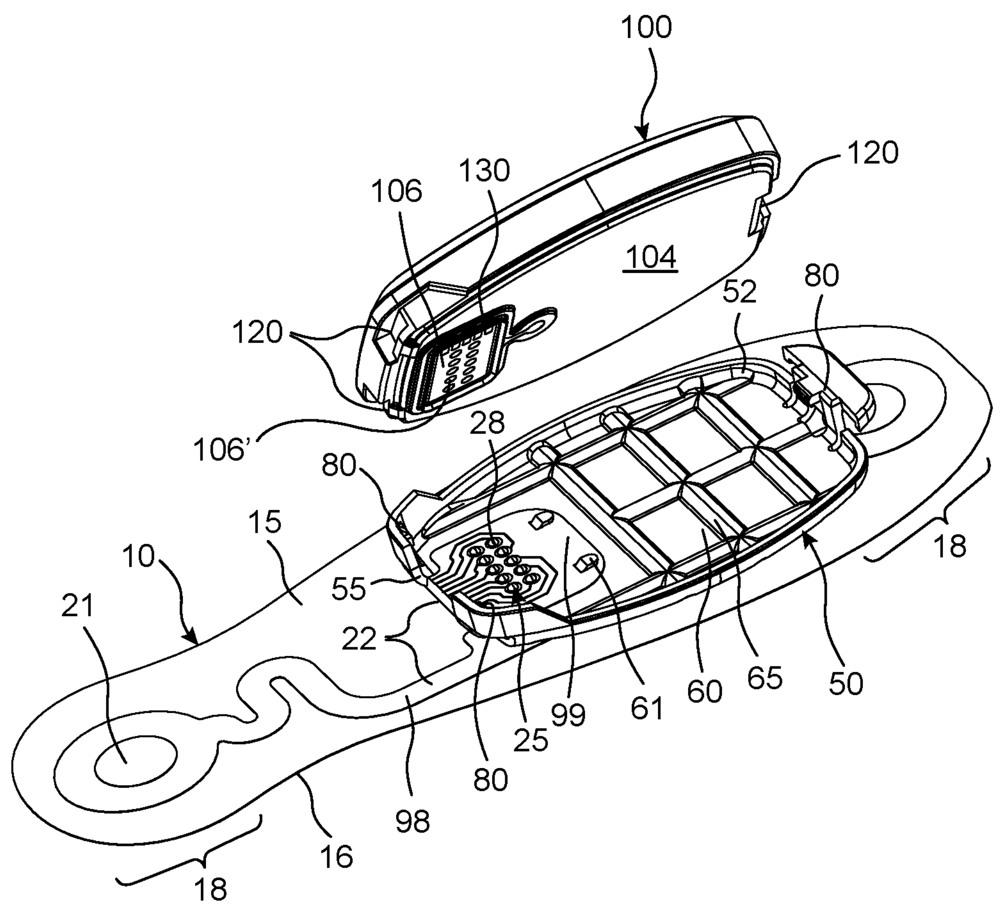
FIG. 1*b* is a view similar to FIG. 1*a*, but showing the monitoring device in a disassembled state.
Figure 1C:
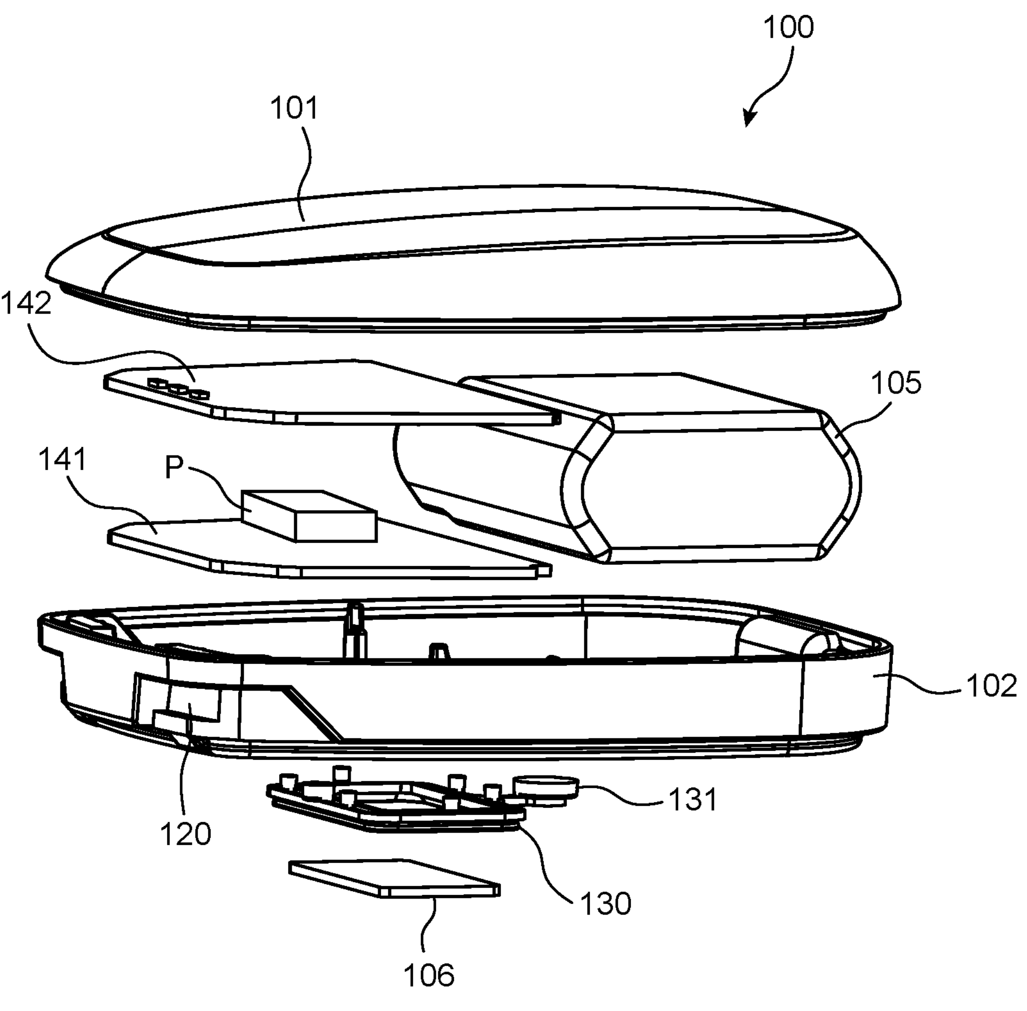
FIG. 1*c* is an exploded perspective view of a housing part of the device.
Figure 1D:
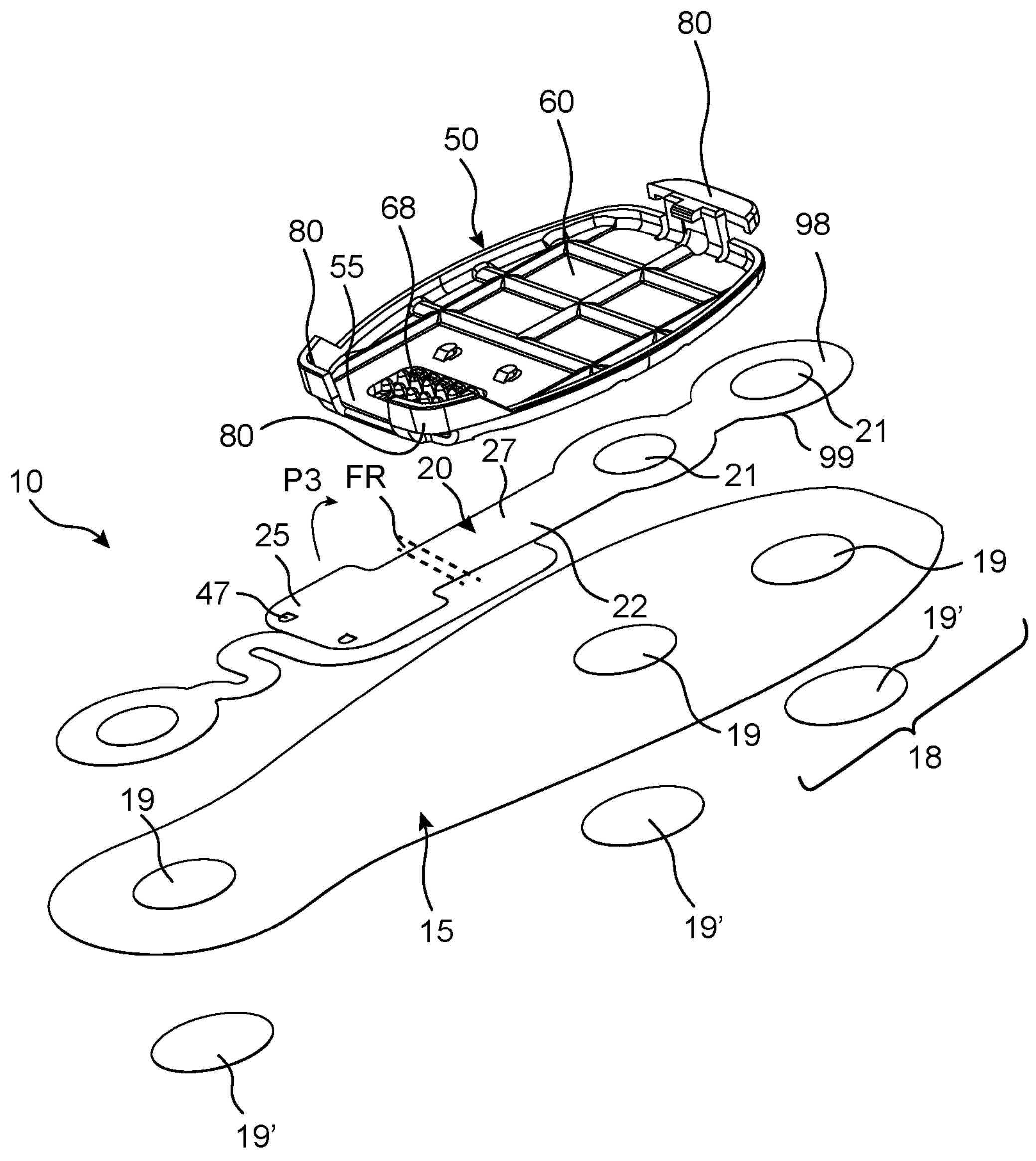
FIG. 1*d* is an exploded perspective view of data collector and socket parts of the device.

The data collector 10 includes several mutually bonded layer, of which only two are shown in FIG. 1*d*, defined by respective flexible sheets of which a first sheet 15 shown in FIG. 1*d* defines a lower or first dermal side surface 16 of the data collector 10. The first sheet 15 may by way of example be defined by a layer of a PET non-woven material, and the first dermal side surface 16 carries a layer of an adhesive material covered by a release liner (not shown in the drawings).

Figure 1E:
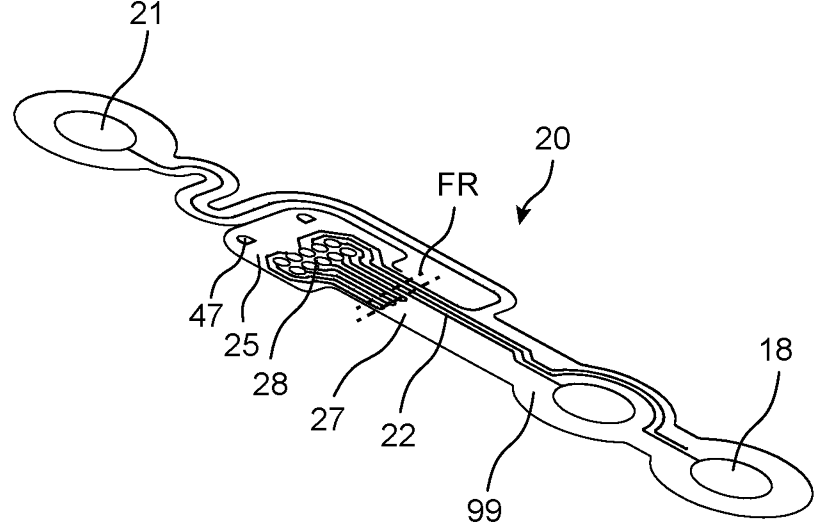
FIG. 1*e* is a perspective bottom view of a second sheet of the data collector of FIG. 1*d,*
Figure 7A:
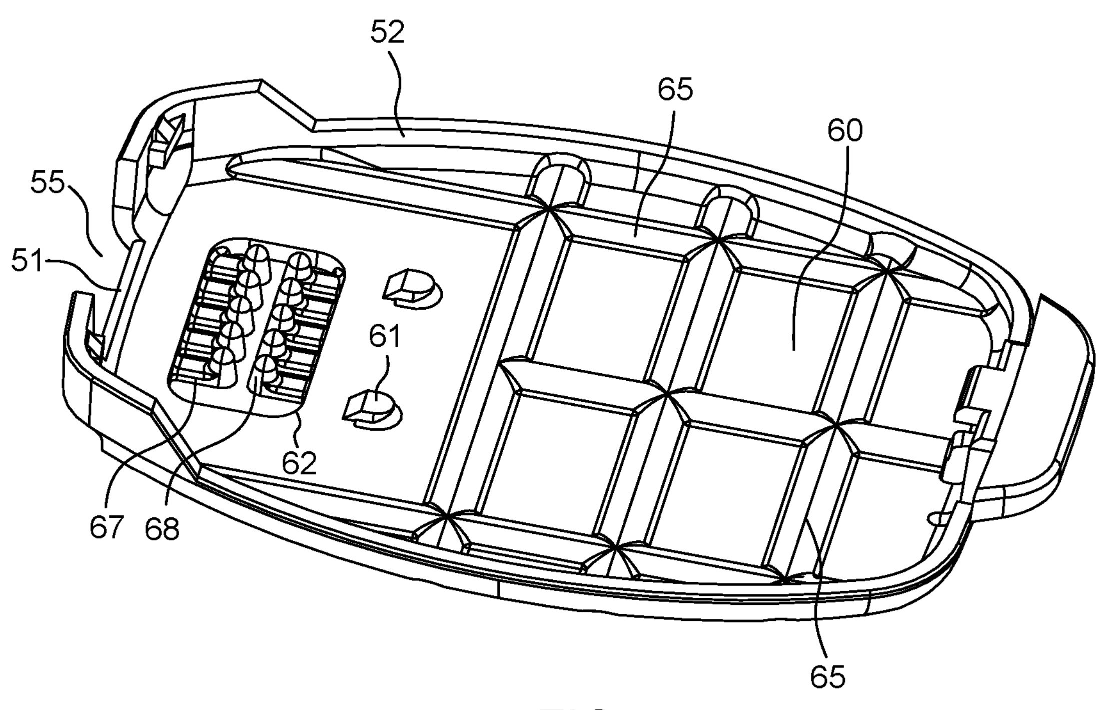
FIGS. 7*a* and 7*b* show perspective views of the socket part of FIG. 1*b*, seen from above and below, respectively.
Figure 7B:
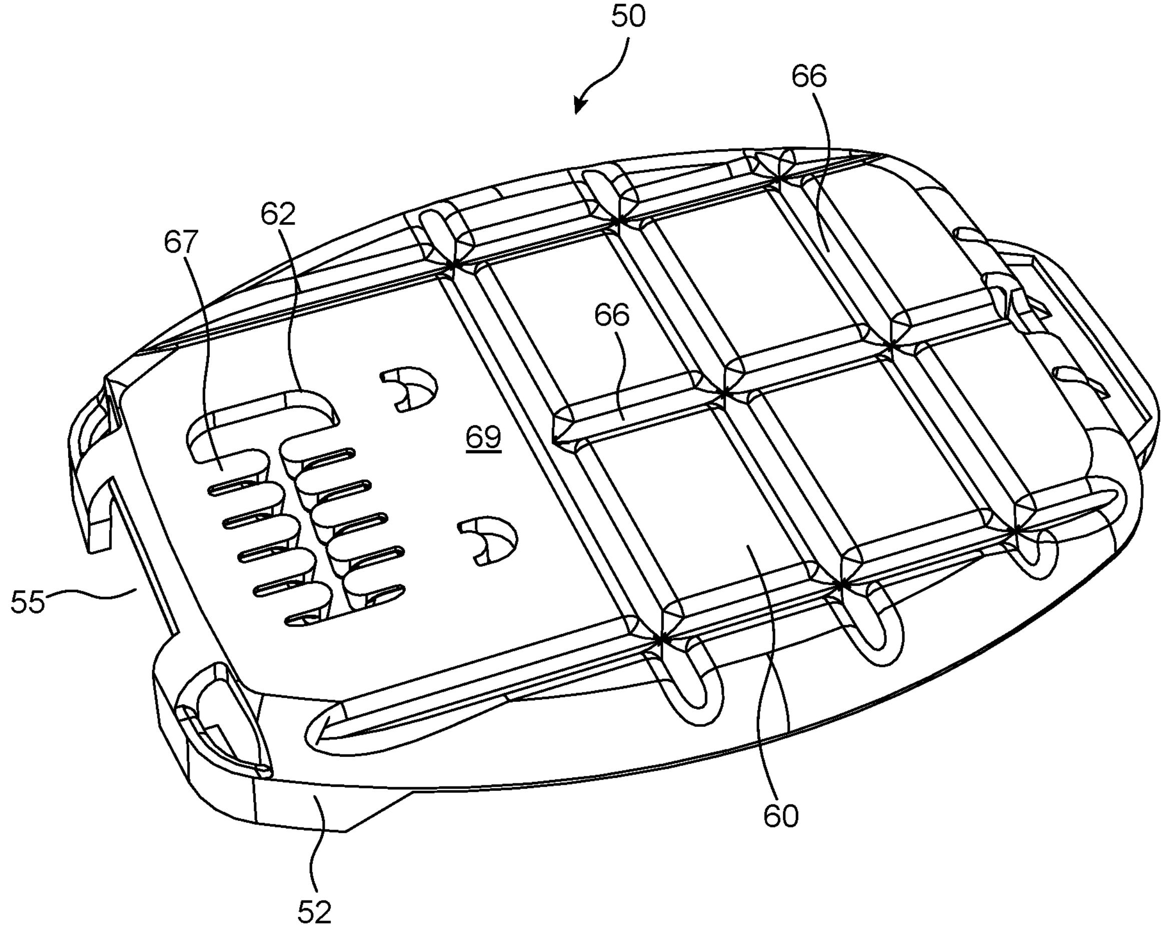

An upper or second surface 17 of the data collector 10 opposite the first dermal side surface 16 is defined by a cover sheet 200 (seen in FIG. 1*a* but not in FIGS. 1*b* and 1*d*) which preferably has a contour corresponding to that of the first sheet 15 and which is adhesively connected to the lower face 69 of a base 60 of the socket 50, see FIG. 7*b*. A second flexible sheet 20, seen best in FIGS. 1*d* and 1*e*, is sandwiched between the first sheet 15 and the cover sheet 200.

By means of the layer of the adhesive material is the first side surface 16 of the data collector 10 attachable to the skin of a person to be monitored, and from the data collector 10 may data captured by the sensing portions 18, 21 be transferred to and collected in the housing 100 via an interface of the monitoring device 1. This data may be stored and processed in the housing 100, and/or the housing 100 may include a transmitter for wired or wireless transmitting of the data as is, or in a processed format, to a remote receiver. The data collector 10 is flexible so it may conform to the skin surface of the person to be monitored.

The present invention aims at maintaining the aforementioned interface sealed against the surroundings while at the same time providing a monitoring device 1 that may easily be manufactured and be assembled by a user with a low manual effort.

In use of monitoring devices 1 is the data collector 10 together with the socket 50 normally replaced at frequent intervals, such as when the data collector has lost its ability to correctly adhere to the person's skin. For this, a user will remove the monitoring device 1 from his skin, disconnect the housing 100 from the socket 50, place a new data collector 10 with a new socket 50 on his skin, and connect the same housing 100 to the new socket 50.

The socket 50 as such is best seen in FIGS. 7*a* and 7*b*, and preferably is defined by a relatively flat, rigid structure molded from a plastics material and defined by the aforementioned base 60 integral with which there may be an upstanding peripheral wall 52. As seen in FIG. 7*b* the base 60 preferably has an open system of interconnected grooves 66 on its lower face 69, opening up at the periphery of the base 60, to allow for any moisture transported from the skin of the person through the layers of the data collector 10, to evaporate at the level of the base 60.

FIG. 1*b* shows the monitoring device 1 in a disassembled state with a base or lower side 104 of the housing 100 being visible. For clarity the cover sheet 200 and any other sheet layers positioned on top of the second sheet 20 of the data collector 1 are not shown.

On the lower side 104 of the housing 100 is a first electrical coupling area 106 of the monitoring device 1, which first electrical coupling area 106 includes electrical terminals 106' arranged for contacting opposed electrical terminals 28' of a second electrical coupling area 28 of the monitoring device 1, namely a second electrical coupling area 28 defined by an interface portion 25 of the second sheet 20. When the monitoring device 1 is in the assembled state shown in FIG. 1*a* the opposed electrical terminals 28', 106' contact each other to define the interface of the monitoring device 1.

The second sheet 20, shown in various embodiments in FIGS. 1*d*-1*g*, generally includes the aforementioned interface portion 25 and a pattern 22 of an electrically conductive material which may be defined by an internal layer of the second sheet 20. The electrically conductive material connects with the electrical terminals 28' of the second electrical coupling area 28 and establishes electrical communication with the sensing portions 18, 21, which may in a simple version be defined by electrodes directly connected with the electrically conductive material defining the pattern 22. Where electrical current is to flow from one surface of the second sheet 20 to an opposite surface this may be by way of so-called "vias" known in the art of PCB's.

As mentioned, the opposed first and second electrical coupling areas 28, 106 with the contacting electrical terminals 28', 106' define the aforementioned interface between the housing 100 and the data collector 10. The interface portion 25 of the second sheet 20 is a portion of the data collector 10 that may be manipulated relative to the remaining portions of the data collector 10 when the latter is connected to the socket 50 in the way that the interface portion 25 may be turned out of the general plane of the data collector 10, as explained further below, and thereby brought to rest against an upper face of the base 60 and secured in that position. In this way is the monitoring device 1 interface located inside the socket 50, protected against mechanical impacts and with the remaining portions of the data collector 10 extending below the base 60 of the socket 50.

In a first embodiment, the second sheet 20 may have the pattern 22 of the electrically conductive material formed on its first or lower side surface 99, as shown in FIGS. 1*b* and 1*e*. In this first embodiment the second sheet 20 has a foldable region FR allowing the interface portion 25 to be folded back by about 180° in the direction shown by the arrow P3 from the position shown in FIGS. 1*d* and 1*e* to the position shown in FIGS. 1*b* and 2*b* where the interface portion 25 is arranged inside the socket 50, resting against the base 60 of the socket 50 and held in place by base 60 tongues 61 entering holes 47 formed in the second sheet 20, with the corresponding portion of the lower side surface 99 facing now upwards. As seen in FIGS. 1*d* and 1*e* a reduced width portion 27 of the second sheet 20 may define the foldable region FR, with the interface portion 25 having a greater width to accommodate the spaced apart electrical terminals 28'.

Figure 2A:
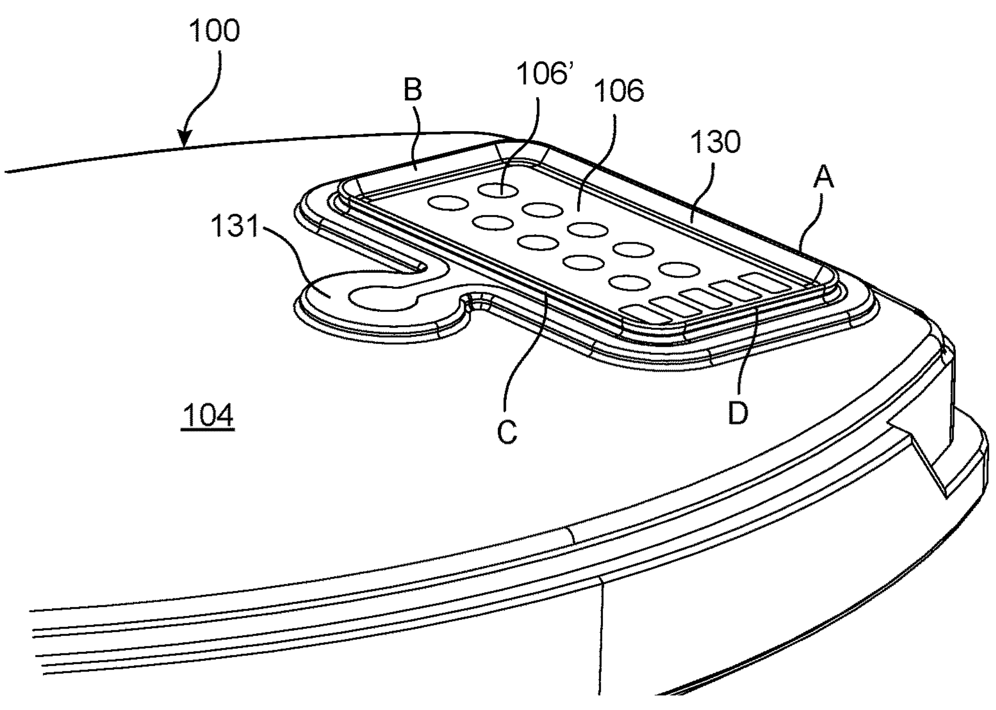
FIG. 2*a* is a perspective enlarged view of a portion of the bottom of the housing part shown in FIG. 1*c,*
Figure 2B:
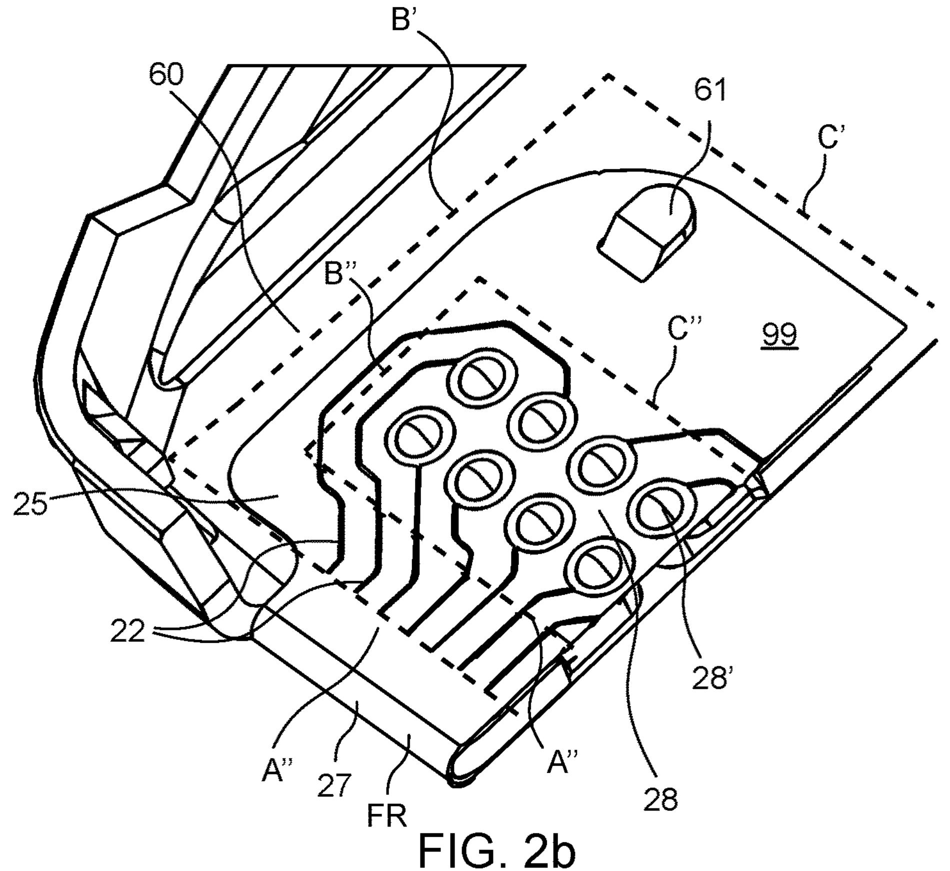
FIG. 2*b* is a perspective enlarged view of a portion of the data collector with the socket part shown in FIG. 1*b,*
Figure 3A:
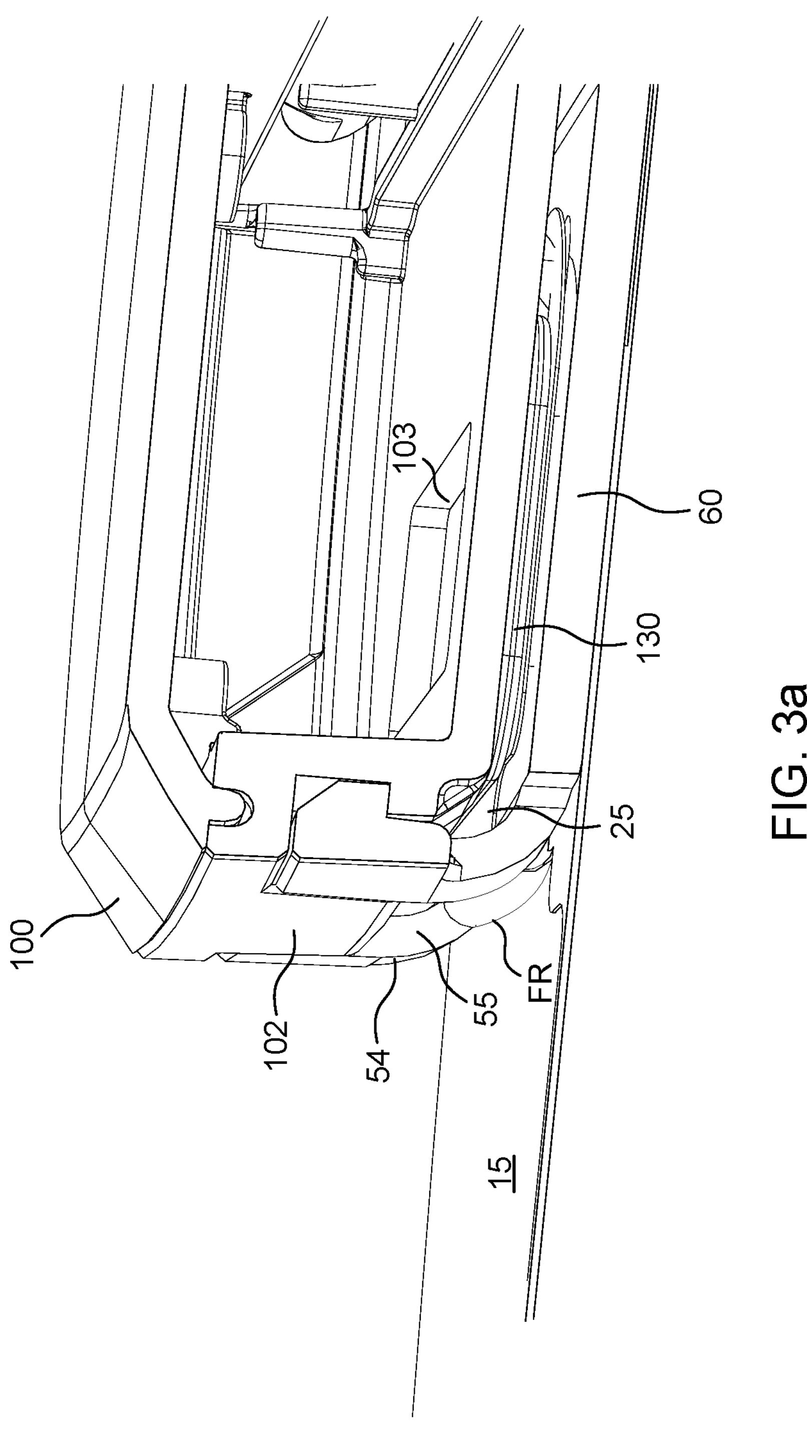
FIG. 3*a* is an enlarged cross-sectional view of a portion of the monitoring device shown in FIG. 1*a*, with some of the components inside the housing part not shown.
Figure 3B:
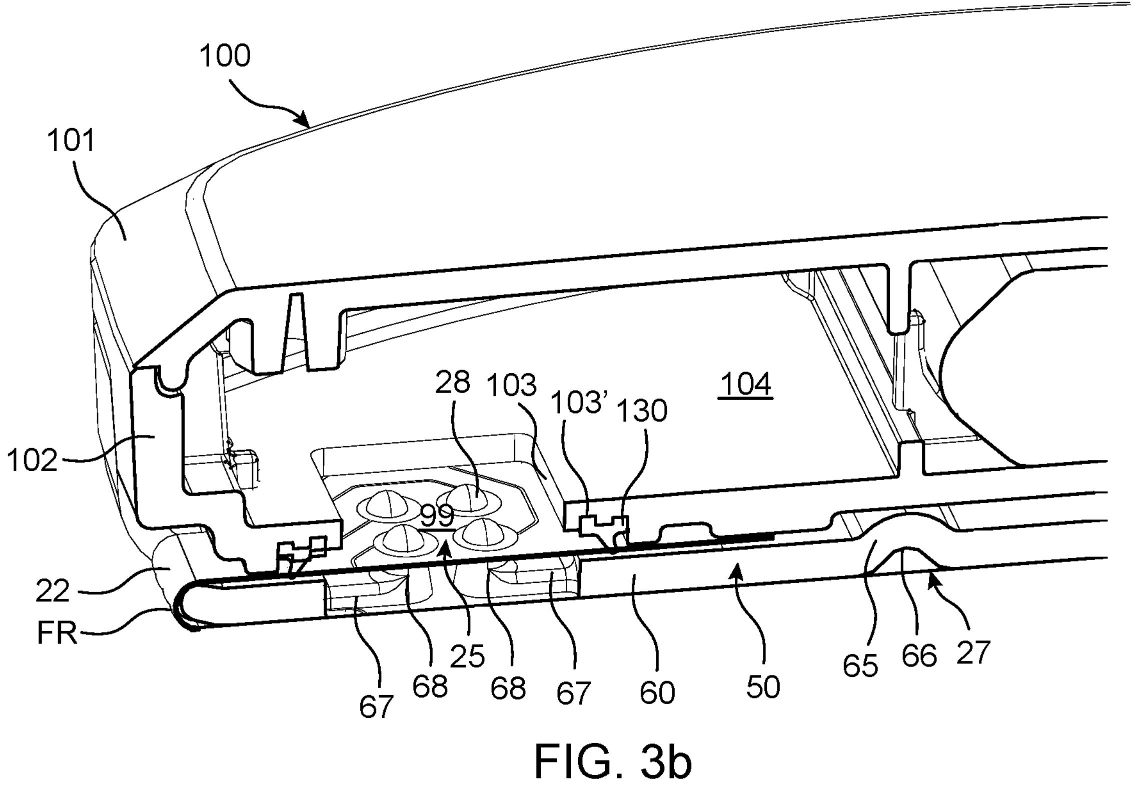
FIG. 3*b* is another view similar to FIG. 3*b,*
Figure 3C:
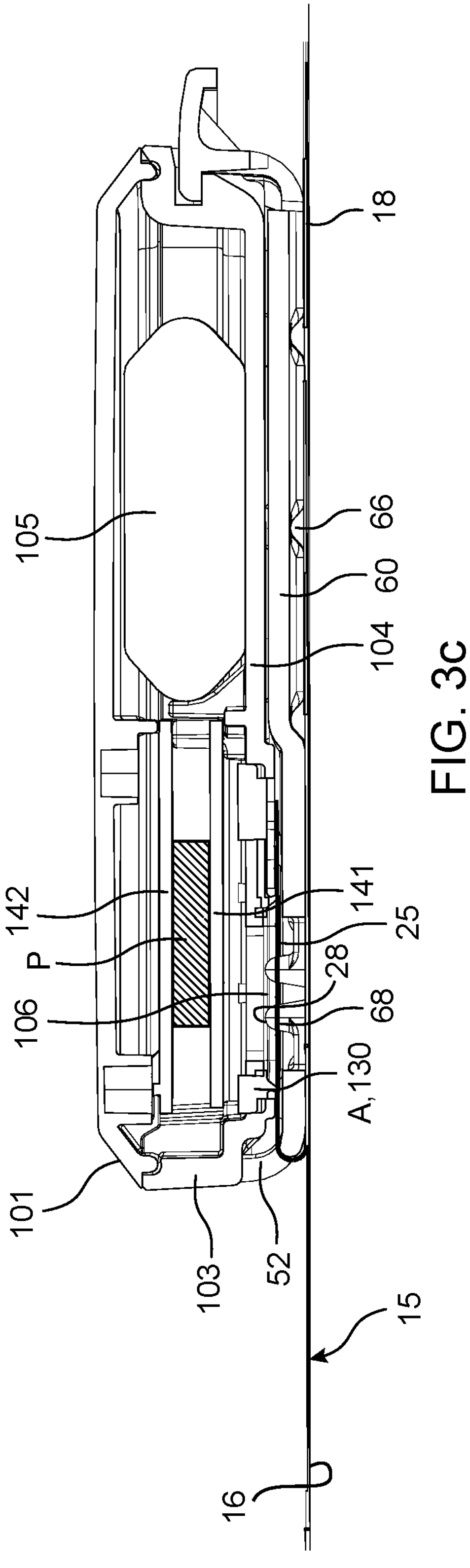
FIG. 3*c* is a cross-sectional side view of the monitoring device of FIG. 1*a,*

It will be understood that in the aforementioned first embodiment is the second sheet 20 in the area of the interface portion 25 disconnected from the subjacent layers to allow for the aforementioned manipulation. Moreover, the portion of the shown upwardly oriented face of the second sheet 20 at the transition to the interface portion 25, illustrated as the reduced width portion 27 seen best in FIG. 2*b*, is preferably provided with a protective cover (not shown).

Figure 1F:
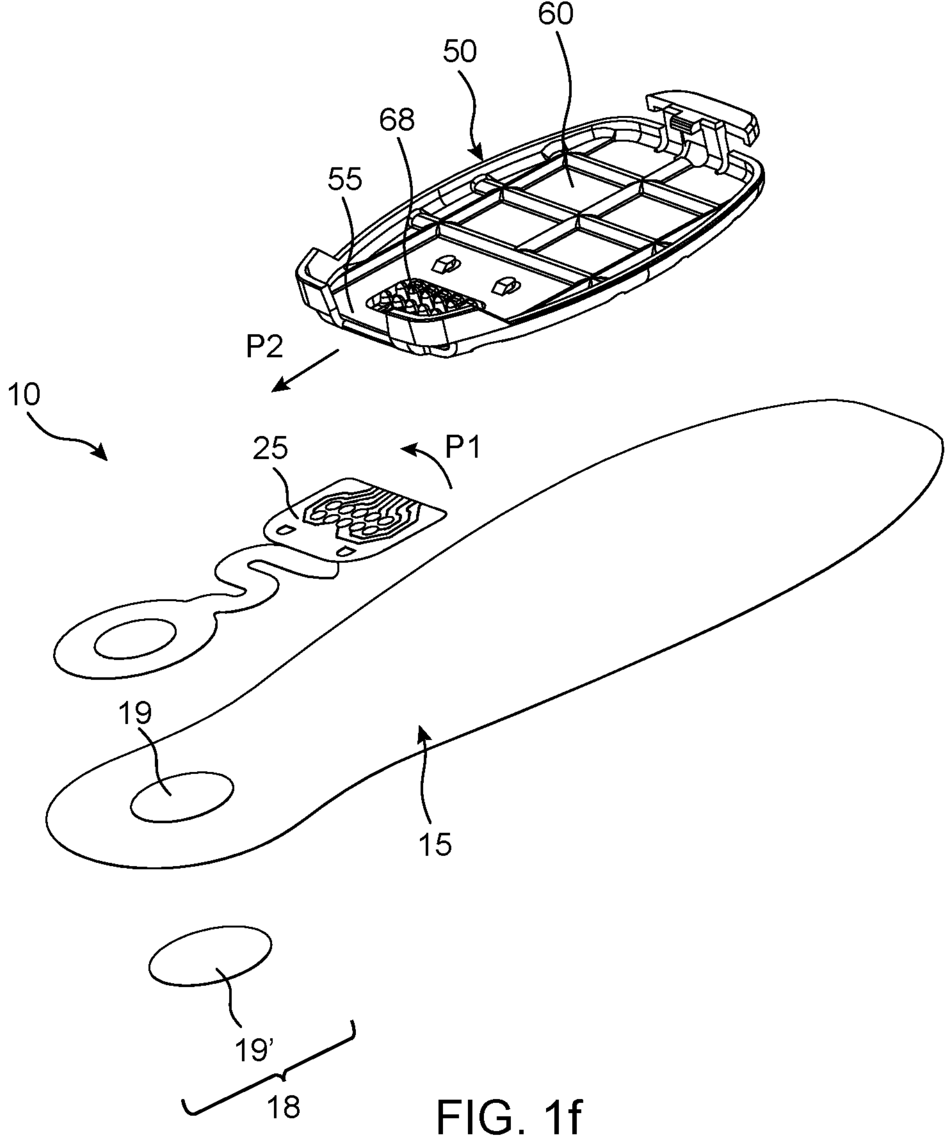
FIG. 1*f* is a view similar to FIG. 1*d*, showing a second embodiment of a data collector part of the device.

In a second embodiment shown in FIG. 1*f* is the second sheet 20 in the area of the interface portion 25 neither covered by the superjacent layer(s) 200 nor connected to the subjacent layer(s) 15. In this embodiment, arranging the interface portion 25 on top of the base 60 is carried out by first turning the free interface portion 25 slightly upwards as indicated by arrow P1 and then moving the socket 50 as indicated by arrow P2, whereafter the socket 50 is adhered to upper surface 17 of the cover sheet 200 (not shown in FIG. 1*f*) of the data collector 1. Also in this case is the shown upwardly oriented portion of the upper face of the second sheet 20 at the transition to the interface portion 25 preferably provided with a protective cover (not shown).

FIG. 1*b* moreover shows the housing 100 having first mechanical connector structures 120 configured for mechanically and releasably engaging second mechanical connector structures 80 of the socket 50. In the shown example the second connector structures 80 at one end of the socket 50 cooperate with first connector structures 120 at the corresponding end of the housing 100 to form a releasable pivotal engagement of the housing 100 with the socket 50 while other connector structures 80, 120 at the corresponding opposite ends (shown to the right in FIG. 1*b*) of the socket 50 and the housing 100 provide a releasable snap engagement between the socket 50 and the housing 100 once the housing in pivotal engagement with the socket 50 has been turned into a position as shown in FIG. 1*a*, in which the snap-engagement is established. Other releasable connection may be foreseen, such as a magnetic connection.

FIG. 1*c* shows the various components of the housing 100, including an upper component 101 and a lower component 102 which has the housing base or lower side 104 that has an aperture at the level of which is mounted an electrical connector plate 141 carrying the first electrical coupling area 106 of the monitoring device 1. Extending around the first electrical coupling area 106, mounted to the base 104 in close proximity to the first electrical coupling area 106, is a sealing gasket 130 formed from a flexible material. The sealing gasket 130 is shown also in FIG. 2*a*, and has a geometrical shape corresponding to the shape of the first electrical coupling area 106, i.e. to narrowly surround the area that has the electrical terminals 106'. In the shown embodiment the gasket 130 is defined by four elongated segments A, B, C, D, and is sized and arranged to abut against the interface portion 25 of the second sheet 20. The housing 100 also may include a processor P mounted to the connector plate 141. Power is provided by the shown battery pack 105.

Figure 4A:
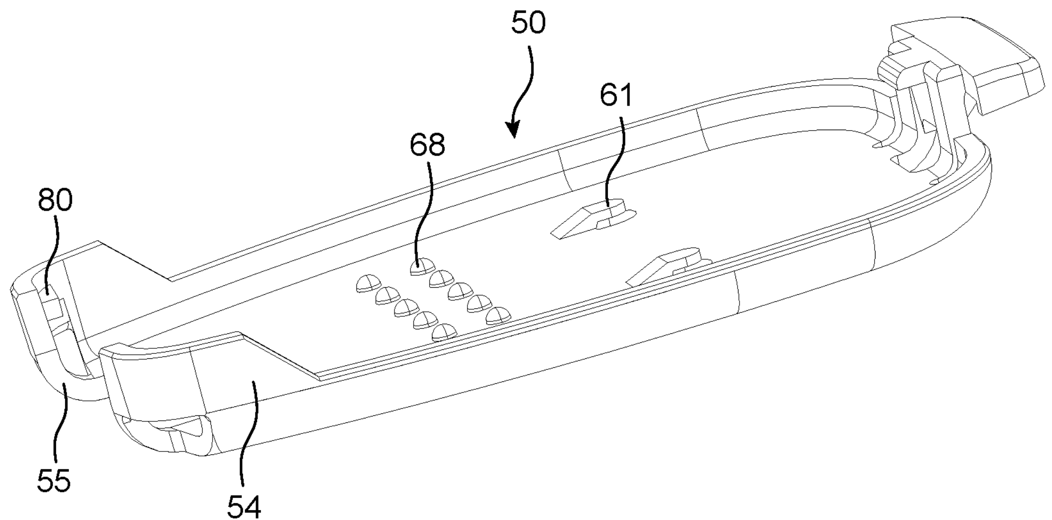
FIG. 4*a* shown one embodiment of a socket part of the monitoring device.
Figure 4B:
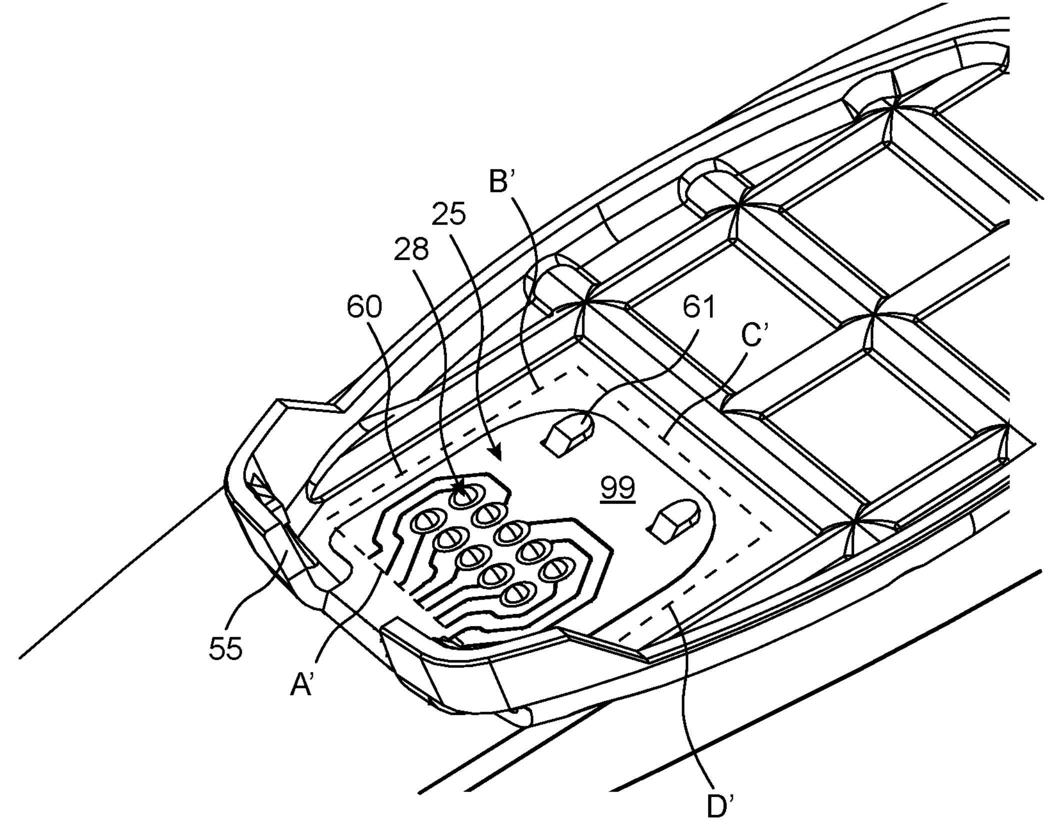
FIG. 4*b* is a view similar to FIG. 2*b,*

FIGS. 2*b* and 4*b* show by broken lines how the housing 100 gasket 130, depending on its shape and in accordance with the invention, is arranged to directly contact and thereby seal against at least one section A" of the interface portion 25, in such a manner that the sealing gasket 130 extends fully around the second electrical coupling area 28 by the rest of the sealing gasket 130 either contacting and sealing against the rest of the interface portion 25 or by the rest of the sealing gasket 130 contacting and sealing against the base 60 of the socket 50. Thus, where the gasket 130 as shown in FIG. 2*a* has a rectangular shape with four segments A, B, C, D the first segment A may contact and seal against one section A" of the interface portion 25 while the remaining segments B, C, D may contact and seal against i) sections B', C', D' of the base 60 of the socket 50 or ii) further sections B", C" (and D" parallel with section B") of the interface portion 25. A round or oval gasket 130 may similarly contact and seal against at least one section A" of the interface portion and sections of the base 60 or of the interface portion 25.

Figure 8:
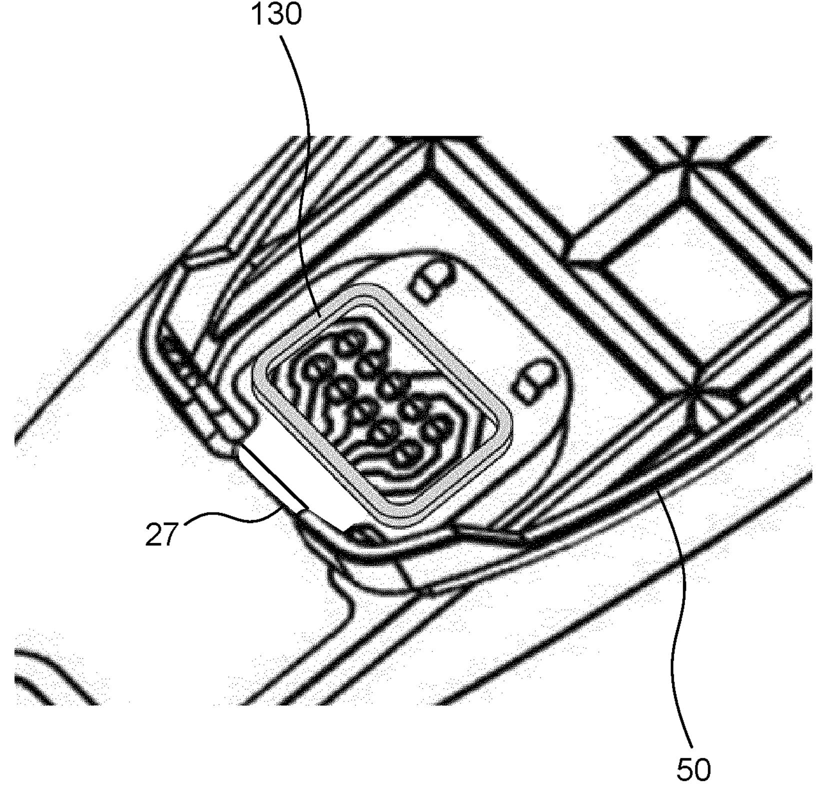
FIG. 8 shows an embodiment where the sealing gasket is in the socket part.

In yet a further embodiment of the invention shown in FIG. 8, that may by way of example highly conveniently be implemented with the second embodiment illustrated in FIG. 1*f*, is the gasket 130 mounted, such as by an adhesive, onto the interface portion 25, to extend around the second coupling area 28, in the way that the gasket 130 is a part of the data collector 20 and not of the housing 100. On connecting the housing 100 to the socket 50 the base or lower side 104 will press against the gasket 130 to establish a tight seal preventing as previously explained moisture ingress where there is electrical connection between the first and second electrical coupling areas 28, 106.

Figure 6:
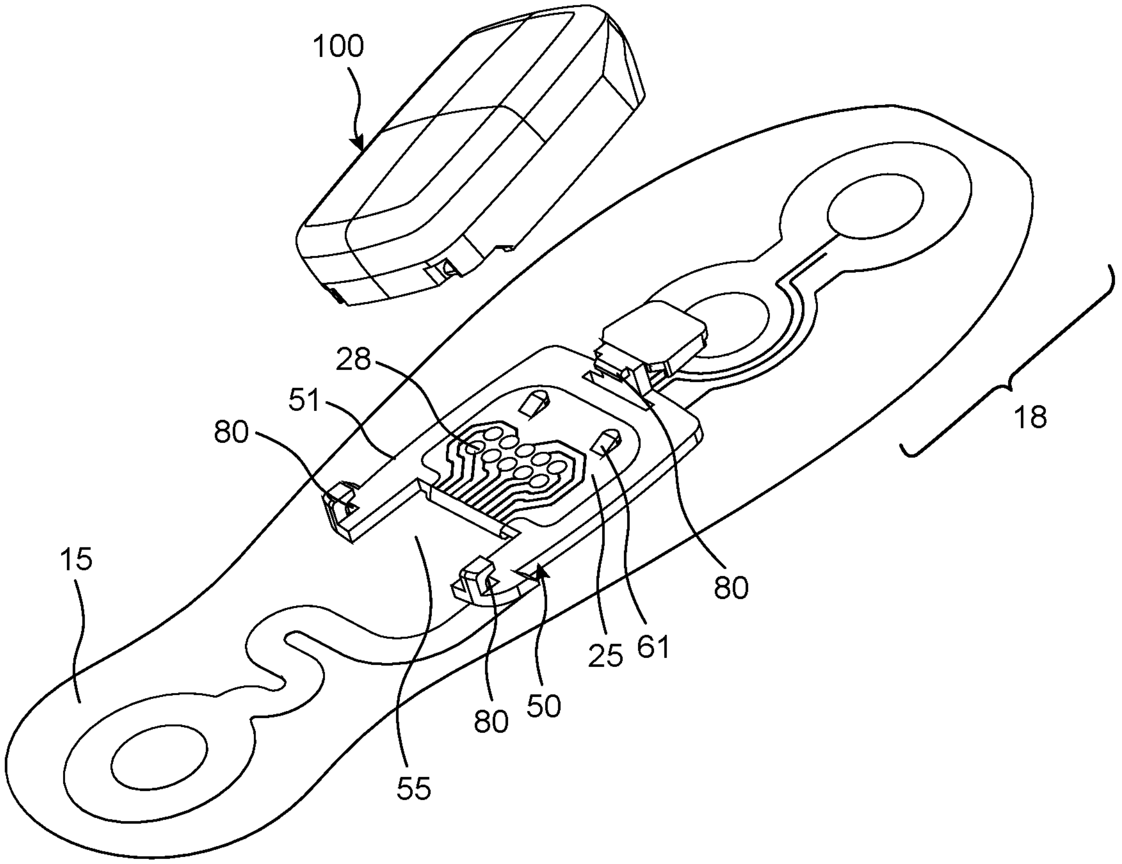
FIG. 6 is a view similar to FIG. 1*b*, showing another embodiment of the socket part.

Common for the embodiments of the socket 50 shown in the drawings is that its base 60 has an edge 51 along its periphery, as shown in FIG. 6, or that the socket 50 includes an upstanding peripheral wall 52 that has a recess 55 that defines a length of an edge 51 along the periphery of the base 60, as seen best in FIG. 7*a*. The transition 27 to the interface portion 25 overlies a portion of this peripheral edge 51, with only a relatively short length or portion 27 of the second sheet 20 required to define the transition to the interface portion 25. Using a recess 55 as shown allows for the interface portion 25 to be positioned on top of the base 60 displaced only slightly inside the socket 50 from its general contour.

Preferably, the interface portion 25, as well as the gasket 130, may be secured to the base 60 so as to be closer to those first and second connector structures 80, 120 discussed above that define together a hinge for pivotal engagement of the housing 100 with the socket 50. This allows for the gasket 130 to be pressed very tightly against the opposing surface to ensure a very high degree of tightness as the housing 100 is turned about the hinge to be locked to the socket 50 by the remaining connector structures 80, 120 engaging each other.

Figure 5:
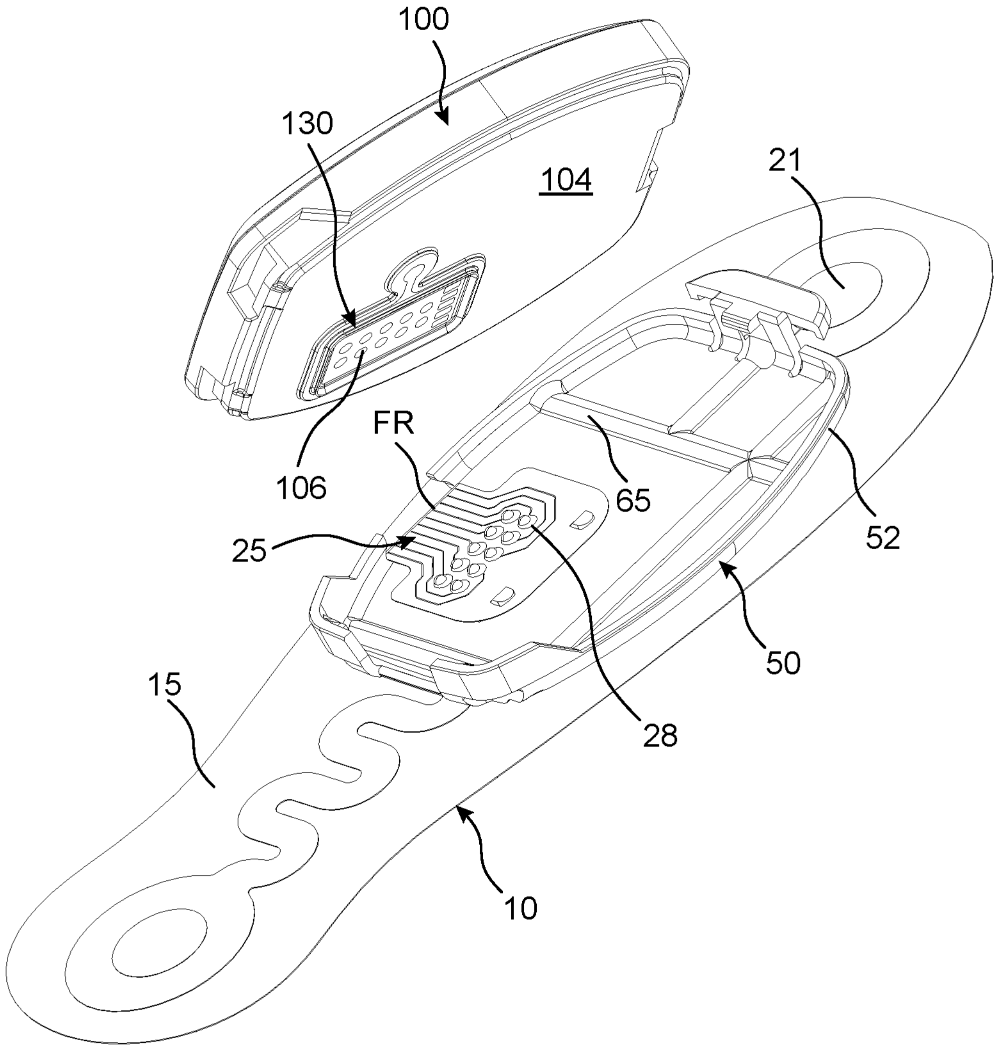
FIG. 5 is a view similar to FIG. 1*b*, showing another embodiment of the socket part.

FIG. 5 is a view similar to FIG. 1*b*, but where the recess is formed in one of the longer sides of the socket 50.

The invention claimed is:

1. A monitoring device comprising (i) a housing with a sealing gasket and (ii) a data collector, the housing with the sealing gasket being releasably connectable to the data collector:

- the housing comprising first connector structures and a base with said sealing gasket and a first electrical coupling area;
- the data collector comprising a first sheet comprising a dermal side surface for adhesion to a skin surface of a subject to be monitored;
- a socket comprising a base and connected to said data collector, said socket comprising second connector structures for said releasably connecting said data collector to said housing via said first connector structures, at least some of said first and second connector structures defining complementary snap-locks;
  - said data collector further comprising a second sheet with a pattern of an electrically conductive material extending between a sensing portion of the data collector and an interface portion of said data collector, which interface portion is arranged in side said socket on said base of said socket, said interface portion comprising a second electrical coupling area for electrically connecting said first electrical coupling area with said sensing portion via said pattern of an electrically conductive material;
- the sealing gasket being so arranged on said base of the housing that it extends around said first electrical coupling area and said second electrical coupling area when the housing is connected to said data collector,
- said sealing gasket contacting at least a first section of said interface portion, and said first and second connector structures pivotably engaging each other to define a hinge.

2. The device of claim 1, said sealing gasket comprising a first segment contacting said first section of said interface portion, and comprising further segments contacting respective sections of said base of said socket.

3. The device of claim 2, said first segment and said further segments of said sealing gasket being elongated.

4. The device according to claim 1, said sealing gasket contacting said interface portion along an entire extension of said sealing gasket.

5. The device of claim 1, said second sheet comprising a foldable region, said interface portion being arranged inside said socket by folding said second sheet along said foldable region.

6. The device of claim 5, a reduced width portion of said second sheet defining said foldable region.

7. The device of claim 1, said socket comprising a peripheral edge with a recess, or said socket comprising an upstanding peripheral wall with a recess.

8. The device of claim 7, a reduced width portion of said second sheet being received in said recess.

9. The device of claim 1, at least some of said first connector structures and said second connector structures being defined by magnets.

10. The device of claim 1, said sensing portion comprising a sensor carried by said second sheet and/or by said first sheet.

11. The device of claim 1, said base of said socket being adhesively connected to a side surface of said data collector opposite said dermal side surface.

12. The device of claim 1, said base comprising a pattern of recesses on a face oriented towards said first sheet.

* * * * *